United States Patent
Nakagawa et al.

(10) Patent No.: US 12,041,330 B2
(45) Date of Patent: Jul. 16, 2024

(54) OPTICAL MODULE FOR ENDOSCOPE AND ENDOSCOPE

(71) Applicant: OLYMPUS CORPORATION, Tokyo (JP)

(72) Inventors: Yusuke Nakagawa, Nagano (JP); Yohei Sakai, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 127 days.

(21) Appl. No.: 17/993,279

(22) Filed: Nov. 23, 2022

(65) Prior Publication Data
US 2023/0083685 A1  Mar. 16, 2023

Related U.S. Application Data

(63) Continuation of application No. PCT/JP2020/024850, filed on Jun. 24, 2020.

(51) Int. Cl.
*H04N 23/54* (2023.01)
*A61B 1/00* (2006.01)
(Continued)

(52) U.S. Cl.
CPC ......... *H04N 23/54* (2023.01); *A61B 1/00165* (2013.01); *A61B 1/051* (2013.01);
(Continued)

(58) Field of Classification Search
CPC ...... H04N 23/54; H04N 23/56; H04N 23/555; G02B 23/2484; G02B 23/26;
(Continued)

(56) References Cited

U.S. PATENT DOCUMENTS

2014/0097459 A1 * 4/2014 Motohara ......... H01L 31/02325
257/432
2018/0353060 A1  12/2018 Miyahara et al.
(Continued)

FOREIGN PATENT DOCUMENTS

EP          2 735 899 A1    5/2014
JP       2013-025092 A      2/2013
(Continued)

OTHER PUBLICATIONS

International Search Report dated Aug. 18, 2020 received in PCT/JP2020/024850.

*Primary Examiner* — Kathleen V Nguyen
(74) *Attorney, Agent, or Firm* — Scully, Scott, Murphy & Presser, P.C.

(57) ABSTRACT

An optical module for endoscope includes a light emitting element, an optical fiber, a ferrule to which the light emitting element is bonded, a wiring board to which the ferrule is bonded, and a resin disposed between the ferrule and the wiring board, wherein the ferrule has a first principal surface made of a transparent material, a second principal surface, and a side surface, the second principal surface has an opening of an insertion hole, the second principal surface has an opening of a groove communicating with the insertion hole, the side surface has an opening of the groove, and a first distance between the opening of the groove on the side surface and the first principal surface is greater than a second distance between the bottom surface of the insertion hole and the first principal surface.

13 Claims, 8 Drawing Sheets

(51) Int. Cl.
  *A61B 1/05* (2006.01)
  *G02B 23/24* (2006.01)
  *G02B 23/26* (2006.01)
  *H04N 23/50* (2023.01)

(52) U.S. Cl.
  CPC ..... *G02B 23/2423* (2013.01); *G02B 23/2461* (2013.01); *G02B 23/2484* (2013.01); *G02B 23/26* (2013.01); *H04N 23/555* (2023.01)

(58) Field of Classification Search
  CPC ............ G02B 23/2461; G02B 23/2423; A61B 1/00013; A61B 1/0011; A61B 1/00165; A61B 1/051
  See application file for complete search history.

(56) References Cited

U.S. PATENT DOCUMENTS

2019/0335068 A1    10/2019  Kato
2020/0000328 A1*  1/2020  Sakai ................ A61B 1/00013

FOREIGN PATENT DOCUMENTS

| | | |
|---|---|---|
| JP | 2019-187806 A | 10/2019 |
| WO | 2017/109930 A1 | 6/2017 |
| WO | 2019/207744 A1 | 10/2019 |
| WO | 2019/208772 A1 | 10/2019 |

* cited by examiner

OPTICAL MODULE FOR ENDOSCOPE AND ENDOSCOPE

CROSS REFERENCE TO RELATED APPLICATION

This application is a continuation application of PCT/JP2020/024850 filed on Jun. 24, 2020, the entire contents of which are incorporated herein by this reference.

BACKGROUND OF THE INVENTION

1. Field of the Invention

The present invention relates to an optical module for endoscope, an underfill resin being disposed between a holder (ferrule) and a wiring board in the optical module, the holder having an insertion hole into which an optical fiber is inserted, a light emitting element being mounted on the wiring board, and to an endoscope including the optical module for endoscope.

2. Description of the Related Art

International Publication No. 2019/208772 discloses an optical module in which a fiber holding portion (ferrule) has a groove, the fiber holding portion having an insertion hole into which an optical fiber is inserted, the groove communicating with the insertion hole. The optical fiber is fixed to the insertion hole with a transparent resin. By injecting a transparent resin into the groove from an opening of the groove on a side surface and by curing the transparent resin, it is possible to efficiently manufacture an optical module having high reliability.

SUMMARY OF THE INVENTION

An optical module for endoscope of an embodiment includes: a light emitting element including a light emitting circuit and an external electrode, the light emitting circuit being configured to convert an image pickup electric signal to an optical signal; a light guide member configured to transmit the optical signal; a holder including a first principal surface, a second principal surface, and a side surface, the first principal surface being made of a transparent material, the second principal surface being disposed on a side opposite to the first principal surface, the holder including a first bonded electrode and a second bonded electrode on the first principal surface, the second bonded electrode being connected to the first bonded electrode, the external electrode of the light emitting element being bonded to the first bonded electrode, the holder including an insertion hole into which the light guide member is inserted, the second principal surface including an opening of the insertion hole, a bottom surface of the insertion hole being made of the transparent material, the holder including a groove communicating with the insertion hole, the second principal surface including an opening of the groove, the side surface including an opening of the groove; a wiring board including a third principal surface, the wiring board including a third bonded electrode on the third principal surface, the third bonded electrode being bonded to the second bonded electrode of the holder; and a resin disposed between the first principal surface of the holder and the third principal surface of the wiring board, wherein in the holder, a first distance between the opening of the groove on the side surface and the first principal surface is greater than a second distance between the bottom surface of the insertion hole and the first principal surface.

An endoscope of an embodiment includes an optical module for endoscope, the optical module for endoscope including: a light emitting element including a light emitting circuit and an external electrode, the light emitting circuit being configured to convert an image pickup electric signal to an optical signal; a light guide member configured to transmit the optical signal; a holder including a first principal surface, a second principal surface, and a side surface, the first principal surface being made of a transparent material, the second principal surface being disposed on a side opposite to the first principal surface, the holder including a first bonded electrode and a second bonded electrode on the first principal surface, the second bonded electrode being connected to the first bonded electrode, the external electrode of the light emitting element being bonded to the first bonded electrode, the holder including an insertion hole into which the light guide member is inserted, the second principal surface including an opening of the insertion hole, a bottom surface of the insertion hole being made of the transparent material, the holder including a groove communicating with the insertion hole, the second principal surface including an opening of the groove, the side surface including an opening of the groove; a wiring board including a third principal surface, the wiring board including a third bonded electrode on the third principal surface, the third bonded electrode being bonded to the second bonded electrode of the holder; and a resin disposed between the first principal surface of the holder and the third principal surface of the wiring board, wherein in the holder, a first distance between the opening of the groove on the side surface and the first principal surface is greater than a second distance between the bottom surface of the insertion hole and the first principal surface.

DETAILED DESCRIPTION OF THE PREFERRED EMBODIMENTS

<Endoscope>

Figure 1:
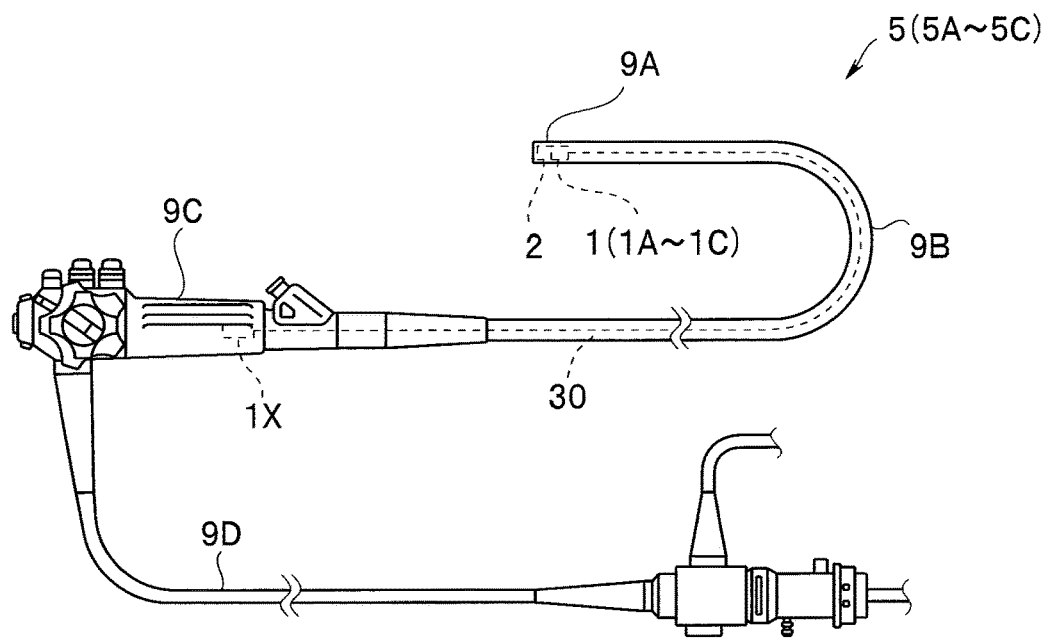
FIG. 1 is a schematic view of an endoscope of an embodiment.

An endoscope 5 of an embodiment shown in FIG. 1 includes an optical module 1 for endoscope (hereinafter also referred to as "optical module") at a distal end portion 9A of an insertion portion 9B.

The endoscope 5 includes the distal end portion 9A, the insertion portion 9B, an operation portion 9C, and a universal cord 9D. An image pickup device 2 and the optical module 1 are disposed at the distal end portion 9A.

An electric signal outputted from the image pickup device 2 is converted to an optical signal by an E/O optical module 1. The optical signal is transmitted to an O/E optical module 1X through an optical fiber 30, the O/E optical module 1X including a light receiving element disposed at the operation portion 9C. The optical signal is converted to an electric signal by the optical module 1X, and is transmitted through metal wiring. That is to say, in the small-diameter insertion portion 9B, a signal is transmitted through the optical fiber 30.

A configuration may be adopted where an optical signal is transmitted through the optical fiber 30 that is inserted through the insertion portion 9B, the operation portion 9C, and the universal cord 9D, and the optical signal is converted to an electric signal by an O/E optical module disposed in a connector of the universal cord 9D or a processor (not shown in the drawing). The processor performs signal processing to allow the electric signal to be displayed on a liquid crystal monitor, for example, as an image.

As will be described later, the optical module has high reliability and high transmission efficiency. Therefore, the endoscope 5 has high reliability and high performance.

The optical module 1X is disposed at the operation portion 9C having a relatively large arrangement space. However, the optical module 1X may have a configuration substantially equal to the configuration of the optical module 1 or the like of the present invention. The endoscope 5 is a flexible endoscope where the insertion portion 9B has flexibility. However, the endoscope 5 may be a rigid endoscope where the insertion portion 9B does not have flexibility in the same manner as the distal end portion 9A. The endoscope 5 may be used as a medical endoscope or an industrial endoscope.

First Embodiment

Figure 2:
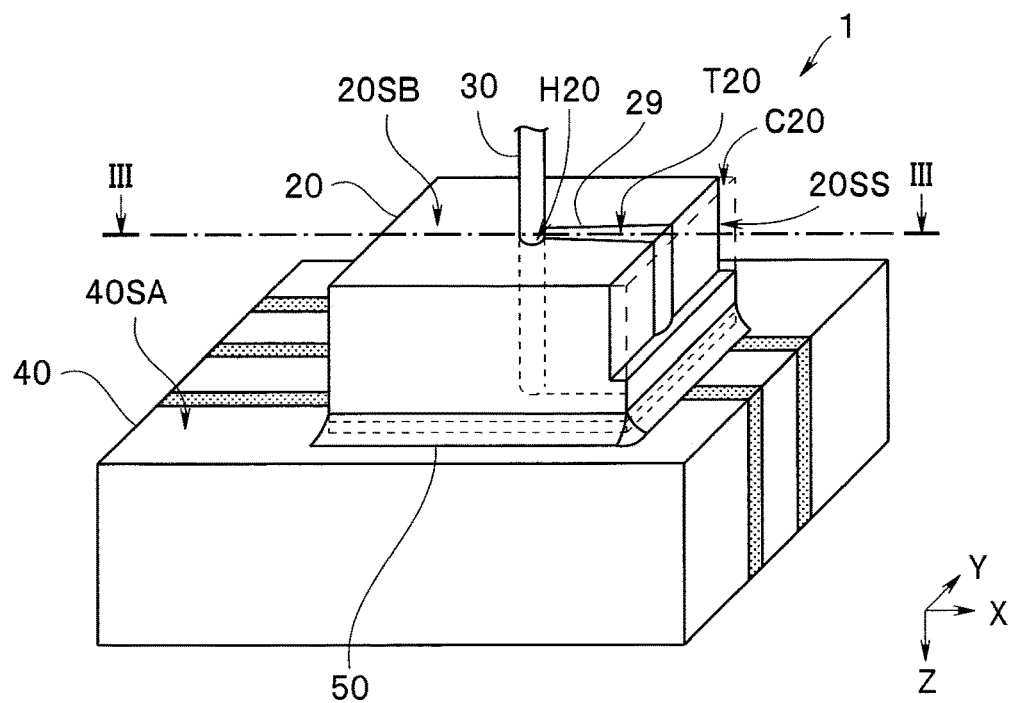
FIG. 2 is a perspective view of an optical module of a first embodiment.

An optical module 1 for endoscope of a first embodiment will be described with reference to FIG. 2 to FIG. 4.

Drawings based on respective embodiments are schematic views. Relationships between thicknesses and widths of respective portions, and ratios or the like between thicknesses of the respective portions, may differ from actual ones. The dimensional relations and the ratios may differ in some parts between drawings. The illustration of and use of reference symbols for some constitutional elements are omitted. To clearly show a structure, the drawings may be inverted vertically. For example, FIG. 4 shows a state where a direction of a Z axis of XYZ orthogonal coordinates is inverted vertically from a state shown in FIG. 2 and FIG. 3.

The optical module 1 is an E/O optical module (electro-optical converter) that converts an image pickup electric signal outputted from the image pickup device 2 of the endoscope 5 to an optical signal and that transmits the optical signal.

The optical module 1 includes a light emitting element 10, the optical fiber 30, a ferrule 20, a wiring board 40, and a resin 50, the optical fiber 30 being a light guide member, the ferrule 20 being a holder that holds the optical fiber 30.

The light emitting element 10 is a VCSEL (vertical cavity surface emitting laser) that outputs an optical signal. As shown in FIG. 4, the light emitting element 10 includes a light emitting circuit 11 and external electrodes 12 connected to the light emitting circuit 11 on a light emitting surface 10SA. The light emitting element 10 has an extremely small size, that is, has a dimension (XY size) of 235 μm×235 μm as viewed in a plan view. The light emitting circuit 11 that outputs an optical signal has a diameter of 10 μm. The external electrode 12 has a diameter of 70 μm.

The optical fiber 30, which transmits an optical signal, includes a core and a clad that covers an outer periphery of the core. A diameter of the core is 62.5 μm. A diameter of the clad is 80 μm.

The ferrule 20 has a first principal surface 20SA, a second principal surface 20SB disposed on a side opposite to the first principal surface 20SA, and a side surface 20SS. The first principal surface 20SA is made of a transparent material. The side surface 20SS is orthogonal to the first principal surface 20SA, for example. The ferrule 20 is a bonded plate obtained by bonding a glass plate 22 and a silicon plate 21, the glass plate 22 being made of a transparent material that forms the first principal surface 20SA, the silicon plate 21 forming the second principal surface 20SB.

The ferrule 20 includes first bonded electrodes 23 and second bonded electrodes 24 on the first principal surface 20SA, each second bonded electrode 24 being connected to a corresponding first bonded electrode 23. Each external electrode 12 of the light emitting element 10 is bonded to a corresponding first bonded electrode 23 using a gold bump 60, for example. A bonded portion between the first bonded electrode 23 and the external electrode 12, that is, a gap formed between the first principal surface 20SA and the light emitting surface 10SA is sealed by a transparent resin 55.

The ferrule 20 has an insertion hole H20 having an opening on the second principal surface 20SB. The insertion hole H20 penetrates through the silicon plate 21, and a bottom surface H20SB of the insertion hole is formed by the glass plate 22, which is made of a transparent material. An inner diameter of the insertion hole H20, 85 μm, is slightly greater than an outer diameter of the optical fiber 30, 80 μm.

The insertion hole H20 is located at a position that faces the light emitting circuit 11 of the light emitting element 10. Therefore, a center axis of the optical fiber 30 inserted into the insertion hole H20 is aligned with an optical axis of the light emitting element 10, so that the optical fiber 30 is optically coupled with the light emitting element 10. The optical fiber 30 inserted into the insertion hole H20 transmits an optical signal generated by the light emitting circuit 11.

The ferrule 20 has an opening (principal surface opening) of a groove (slit, path) T20 on the second principal surface 20SB, the groove extending from the insertion hole H20. The groove T20 extends to the side surface 20SS of the ferrule 20. That is to say, the groove T20 also has an opening (side surface opening) on the side surface 20SS.

As will be described later, the optical fiber 30 is fixed by a UV-curable transparent resin 29 injected from the groove T20. That is to say, the transparent resin 29 is disposed between the insertion hole H20 and the optical fiber 30 and in the groove T20. The transparent resin 29 disposed between the insertion hole H20 and the optical fiber 30 is disposed in a slight gap formed between a wall surface of the insertion hole H20 and an outer surface of the optical fiber 30 and hence, the illustration of such a transparent resin 29 is omitted.

In an extremely small-sized optical module, it is not easy to perform an operation of fixing an optical fiber to a ferrule with an adhesive agent. That is to say, it is not easy to irradiate the transparent resin 29 disposed in the slight gap formed between the wall surface of the insertion hole H20 and the outer surface of the optical fiber 30 with ultraviolet rays in order to cure the transparent resin 29. When the transparent resin 29 is not sufficiently cured, the optical fiber is not sufficiently fixed, so that there is a possibility of a reduction in reliability of the optical module. Further, when air bubbles remain at the time of injecting an uncured transparent resin 29 into the insertion hole H20, transmission efficiency of the optical module is reduced.

In the ferrule 20, the second principal surface 20SB has not only the opening of the insertion hole H20 but also the principal surface opening of the groove T20, and the side surface 20SS has the side surface opening of the groove T20. Ultraviolet rays entering from at least either one of the second principal surface 20SB or the side surface 20SS pass through the transparent resin 29 disposed in the groove T20, and then reach the transparent resin 29 in the insertion hole H20. Therefore, it is possible to apply sufficient curing treatment to the transparent resin 29 in the insertion hole H20, the transparent resin 29 fixing the optical fiber 30. Further, the uncured transparent resin 29 is injected into the insertion hole H20 from the groove T20 and hence, there is no possibility of air bubbles remaining in the transparent resin 29.

As already described above, the optical module 1 includes the wiring board 40 on which the ferrule 20 is mounted. The wiring board 40 is a molded interconnect device (MID) in which wiring and electrodes are formed on a surface of a resin molded product by using a conductor film, such as a plating film. The wiring board 40 has a third principal surface 40SA. The second bonded electrodes 24 on the first principal surface 20SA of the ferrule 20 are bonded to third bonded electrodes 41 on the third principal surface 40SA of the wiring board 40 by solders 65, for example. The light emitting element 10 is accommodated in a hole H40 of the wiring board 40, being a three-dimensional wiring board.

The resin 50, being an underfill, is disposed at bonded portions between the second bonded electrodes 24 and the third bonded electrodes, that is, disposed between the first principal surface 20SA of the ferrule 20 and the third principal surface 40SA of the wiring board 40. To prevent leakage of light from the light emitting element 10, it is preferable that the resin 50 be a light-shielding resin.

The resin 50 not only seals the bonded portions between the second bonded electrodes 24 and the third bonded electrodes, but also causes the ferrule 20 to adhere to the wiring board 40. When a large amount of the resin 50 is used to ensure reliability of the optical module 1, the resin 50 overflows from a gap formed between the first principal surface 20SA and the third principal surface 40SA, and covers a portion of the side surface 20SS.

Figure 3:
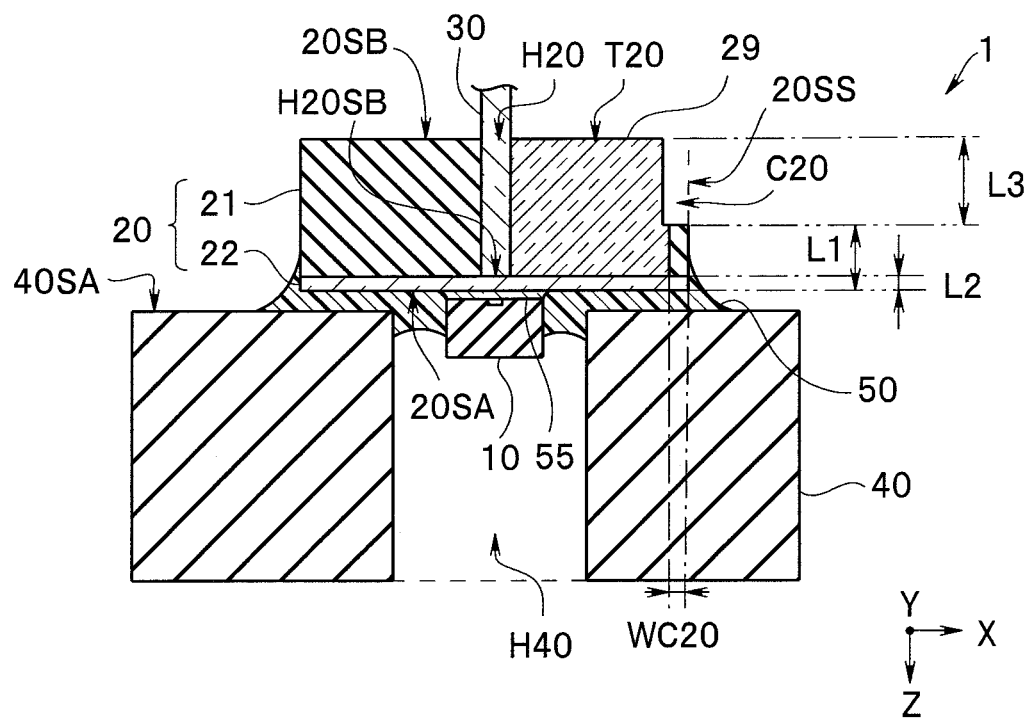
FIG. 3 is a cross-sectional view taken along line in FIG. 2.

As shown in FIG. 3, the ferrule 20 has an opening of the groove T20 within a cutout C20 on the side surface 20SS, the cutout C20 being formed on the silicon plate 21. That is to say, a size of the opening (side surface opening) of the groove T20 on the side surface 20SS is reduced by a wall of the silicon plate 21 on the side surface 20SS.

A first distance L1 between the opening of the groove T20 on the side surface 20SS and the first principal surface 20SA is greater than a second distance L2 between a bottom surface H20SB of the insertion hole H20 and the first principal surface 20SA. The second distance L2 is a thickness of the glass plate 22. A third distance L3 is a depth of the cutout C20. That is to say, a sum of the first distance L1 and the third distance L3 is a thickness of the ferrule 20. Further, a difference between the first distance L1 and the second distance L2 is a height of the wall of the silicon plate 21 on the side surface 20SS.

As will be described later, even when the uncured resin 50 disposed in the gap formed between the ferrule 20 and the wiring board 40 overflows from the gap and spreads out onto the side surface 20SS, the wall of the silicon plate 21 is provided to the side surface 20SS and hence, there is no possibility of the resin 50 intruding into the groove T20.

A height of the side surface opening from the first principal surface 20SA, that is, a preferred length for the first distance L1 shown in FIG. 3 was obtained by experiments. When an uncured thermosetting epoxy resin (the resin 50) was injected between the first principal surface 20SA and the third principal surface 40SA, the resin 50 protruded onto the side surface 20SS, thus forming a fillet. A distance (a height of the fillet) from the first principal surface 20SA to an upper end of the resin 50 was measured. As a result of a plurality of experiments, a maximum height of the fillet was 100 μm. Accordingly, the first distance L1 is preferably more than 100 μm, and is particularly preferably more than 150 μm.

When the first distance L1 is more than the above-mentioned range, there is no possibility of the resin 50 intruding into the groove T20. Further, an opening length L3 of the side surface opening is preferably more than 50 μm, and particularly preferably more than 100 μm. When the opening length L3 is more than the above-mentioned range, the transparent resin 29 can be easily injected from the side surface opening, and can be easily irradiated with ultraviolet rays from the side surface opening. A thickness WC20 of the wall of the silicon plate 21 on the side surface 20SS is preferably more than 50 μm, and is particularly preferably more than 100 μm. The thickness WC20 of more than the above-mentioned range can ensure mechanical strength.

In the optical module 1, it is possible to easily perform an operation of fixing the optical fiber 30 to the ferrule 20 with the transparent resin 29 and hence, the optical module 1 has high reliability.

Further, in the optical module 1, there is no possibility that light generated by the light emitting element 10 is blocked by the resin 50 and that a distance between the light emitting element 10 and a distal end surface of the optical fiber 30 is increased due to the resin 50. Accordingly, the optical module 1 has high transmission efficiency.

<Method for Manufacturing Optical Module for Endoscope>

Next, a method for manufacturing the optical module 1 will be described.

<Step S10> Ferrule Preparation Step

A silicon wafer 21W and a glass wafer 22W are anodically bonded together, for example, to prepare a bonded wafer 20W. An etching mask M20 (not shown in the drawing) is disposed on a second principal surface 20SB of the bonded wafer 20W.

Figure 5A:
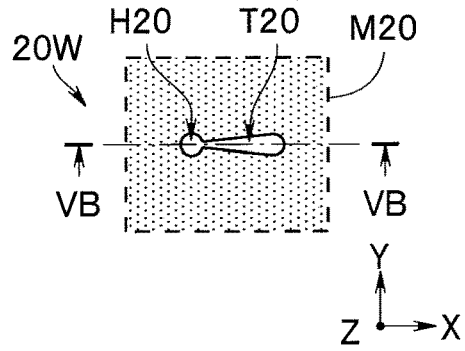
FIG. 5A is a top view for describing a method for manufacturing a ferrule of the optical module of the first embodiment.
Figure 5B:
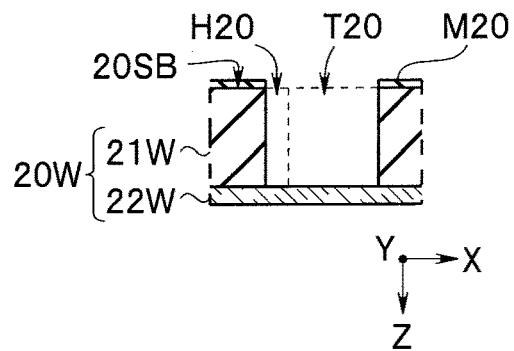
FIG. 5B is a cross-sectional view taken along line VB-VB in FIG. 5A.

Next, as shown in FIG. 5A and FIG. 5B, an insertion hole H20 and a groove T20 are formed by reactive ion etching (RIE), a wall surface of the insertion hole H20 and a wall surface of the groove T20 being substantially perpendicular to the second principal surface 20SB. The glass wafer 22W serves as an etching stop layer and hence, the glass wafer 22W forms a bottom surface of the insertion hole H20 and a bottom surface of the groove T20. The glass wafer 22W may be a resin wafer made of a transparent resin.

In a case where an inner diameter of the insertion hole H20 is 85 µm, a width of the groove T20 is 50 µm at a side surface opening, and is 30 µm at a connection portion with the insertion hole H20. To stably hold the optical fiber 30 inserted into the insertion hole H20, it is sufficient that the width of the groove T20 at the connection portion to the insertion hole H20 be less than the inner diameter of the insertion hole H20. However, it is preferable that the width of the groove T20 at the connection portion with the insertion hole H20 be 80% or less of the inner diameter of the insertion hole H20.

To stably hold the optical fiber 30, it is preferable that a thickness of the silicon wafer 21W (the silicon plate 21) be more than 300 µm.

When a thickness of the glass wafer 22W (the glass plate 22) is less than 50 µm, 95% or more of light at a wavelength of an optical signal passes through the glass wafer 22W and hence, high transmission efficiency can be obtained. When the glass wafer 22W has a thickness of more than 5 µm, the glass wafer 22W is less likely to be broken in a manufacturing process.

An inner surface shape of the insertion hole H20 may be a substantially columnar shape, a polygonal prism shape, or other shapes provided that the insertion hole H20 can hold the optical fiber 30.

Figure 6A:
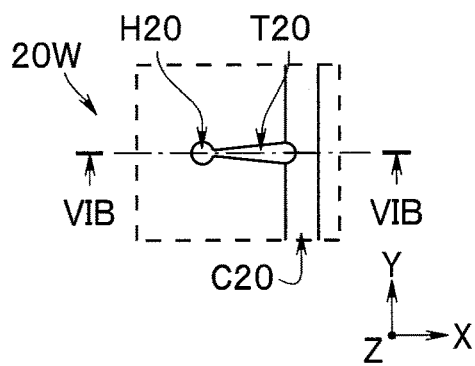
FIG. 6A is a top view for describing the method for manufacturing the ferrule of the optical module of the first embodiment.
Figure 6B:
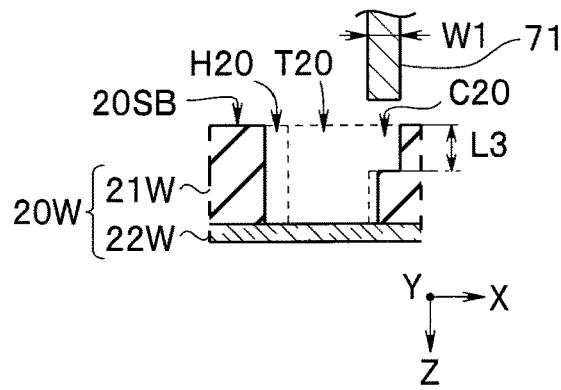
FIG. 6B is a cross-sectional view taken along line VIB-VIB in FIG. 6A.

As shown in FIG. 6A and FIG. 6B, a cutout C20 is formed at an end portion of the groove T20 on the second principal surface 20SB of the bonded wafer 20W by using a first dicing saw 71 having a width (to be more precise, a cutting margin) W1. A depth of the cutout C20 corresponds to the third distance L3 shown in FIG. 3.

Figure 7A:
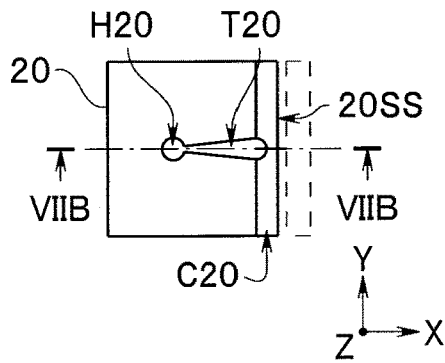
FIG. 7A is a top view for describing the method for manufacturing the ferrule of the optical module of the first embodiment.
Figure 7B:
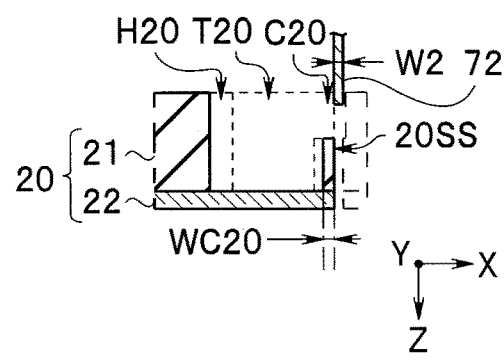
FIG. 7B is a cross-sectional view taken along line VIIB-VIIB in FIG. 7A.

As shown in FIG. 7A and FIG. 7B, the bonded wafer 20W is cut along a cutting line including a bottom surface of the cutout C20 by using a second dicing saw 72 having a width (to be more precise, a cutting margin) W2. The width W2 of the second dicing saw 72 is less than the width W1 of the first dicing saw 71. That is to say, the side surface 20SS of the ferrule 20 is a cut surface formed by cutting the bonded wafer 20W with the second dicing saw 72.

Figure 8:
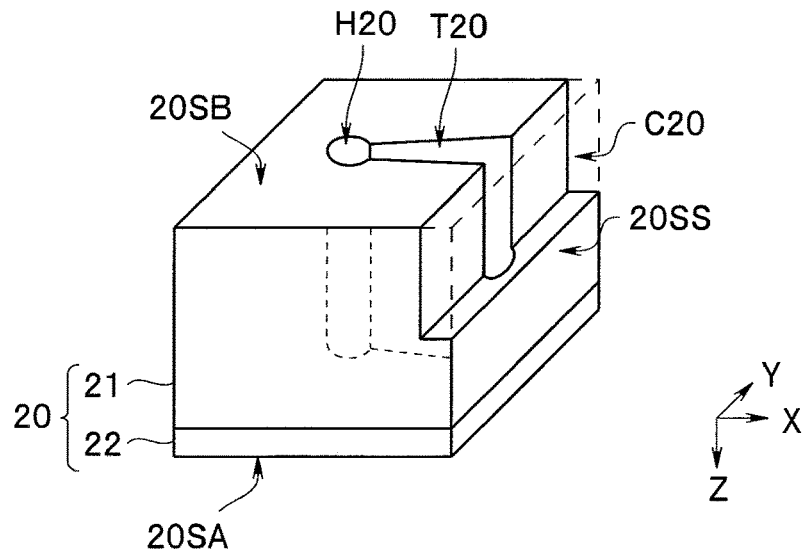
FIG. 8 is a perspective view of the ferrule of the optical module of the first embodiment.

By cutting the bonded wafer 20W with the first dicing saw 71 and the second dicing saw 72, it is possible to prepare the ferrule 20, shown in FIG. 8, that has the cutout C20 on the side surface 20SS.

<Step S20> Light Emitting Element Mounting Step

The light emitting element 10 is mounted on the first principal surface 20SA of the ferrule 20.

Figure 4:
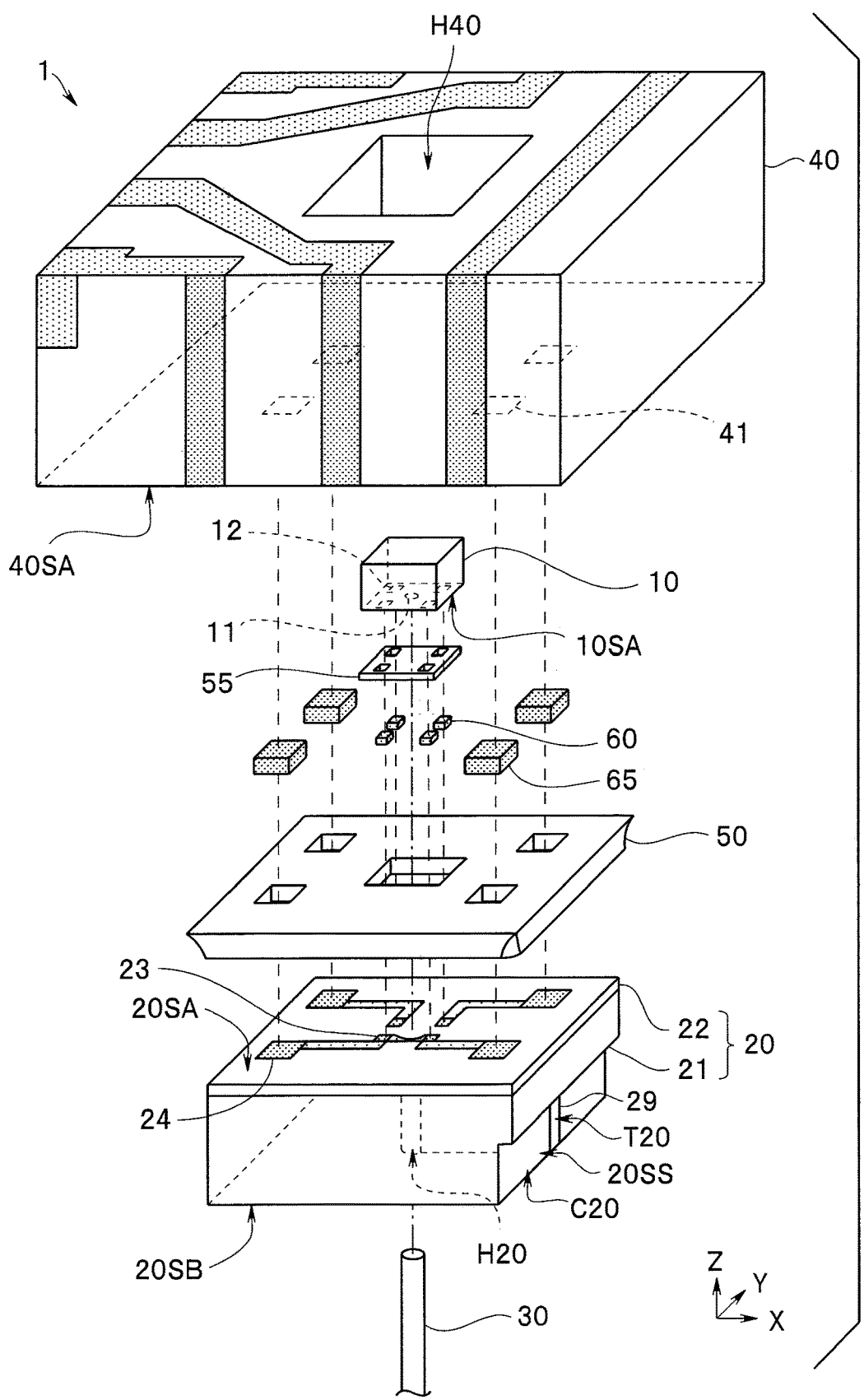
FIG. 4 is a perspective exploded view of the optical module of the first embodiment.

The external electrodes 12 of the light emitting element 10 (for example, the gold bumps 60) are ultrasonically bonded to the first bonded electrodes 23 of the ferrule 20 (see FIG. 4). The light emitting circuit 11 of the light emitting element 10 is fixed at a position that faces the insertion hole H20.

To improve reliability of each bonded portion between the external electrode 12 and the first bonded electrode 23, the transparent resin 55 is disposed in a 15 µm gap formed between the first principal surface 20SA and the light emitting surface 10SA. The transparent resin 55 having high optical transparency may be a thermosetting or a UV-curable silicone resin or epoxy resin, for example.

<Step S30> Wiring Board Bonding Step

The third bonded electrodes 41 on the third principal surface 40SA of the wiring board 40 are bonded to the second bonded electrodes 24 on the first principal surface 20SA of the ferrule 20 by the solders 65, for example (see FIG. 4). A separation between the third principal surface 40SA and the first principal surface 20SA is 50 µm. The light emitting element 10 having a height (a dimension in a Z direction) of 150 µm is accommodated in the hole H40 of the ferrule 20.

Electronic components (a chip capacitor, a signal processing IC, and the like) may be mounted on a surface, a recessed portion, or the like of the wiring board 40, being an MID. The image pickup device 2 may be mounted on the wiring board 40. The electronic components may be incorporated in the wiring board 40.

<Step S40> Sealing Resin Disposing Step

Figure 9:
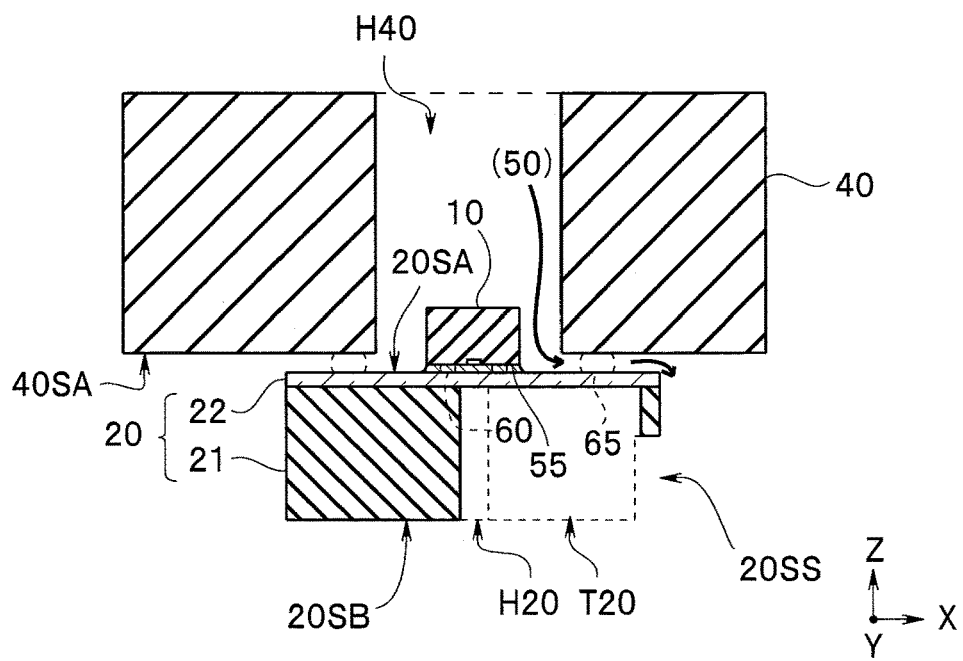
FIG. 9 is a cross-sectional view for describing injection of a resin into the optical module of the first embodiment.

As shown in FIG. 9, an uncured resin 50 is injected into a gap formed between the third principal surface 40SA and the first principal surface 20SA from the hole H40 of the ferrule 20. The resin 50 is selected from various kinds of curing resin. To prevent leakage of light from the light emitting element 10, it is preferable that the resin 50 be a light-shielding resin. An example of the resin 50 includes a thermosetting resin, and a thermosetting epoxy resin may be used as the resin 50, for example. Curing treatment may be applied to the resin 50 at any timing.

There may be a case where the uncured liquid resin 50 overflows from the gap formed between the first principal surface 20SA and the third principal surface 40SA and spreads out onto the side surface 20SS of the ferrule 20. When the resin 50 intrudes into the groove T20 and reaches the insertion hole H20, an amount of light of an optical signal that is incident on the optical fiber 30 is reduced.

In the optical module 1, even when the resin 50 overflows from the gap and spreads out onto the side surface 20SS, the wall of the silicon plate 21 is provided to the side surface 20SS. Therefore, there is no possibility of the resin 50 intruding into the groove T20.

Illustration of following steps will be omitted.

<Step S50> (Uncured) Transparent Resin Injection Step

The uncured liquid transparent resin 29 is injected from the groove T20 of the ferrule 20, so that the transparent resin 29 is disposed in the groove T20 and the insertion hole H20.

The transparent resin 29 is injected into the groove T20 from the side surface opening with the side surface 20SS facing upward, for example. The transparent resin 29 flows into the insertion hole H20 from the side surface through the groove T20, being a flow passage, and hence, there is no possibility of air bubbles remaining in the transparent resin 29.

The transparent resin 29 having high optical transparency may be a UV-curable or a UV- and thermosetting silicone resin or epoxy resin, for example.

<Step S60> Optical Fiber Insertion Step

The optical fiber 30 is inserted into the insertion hole H20.

When the optical fiber 30 is inserted into the insertion hole H20 into which the transparent resin 29 is injected, there is a possibility of the glass plate 22 being broken. A reason is that a pressure is applied to the glass plate 22 by the transparent resin 29 pushed by the optical fiber 30.

In the manufacturing method of the present embodiment, the transparent resin 29 pushed out overflows from the opening of the groove T20. Therefore, when the optical fiber 30 is inserted into the insertion hole H20, there is no possibility of the thin glass plate 22 being broken due to a pressure of insertion.

<Step S70> Transparent Resin Curing Step

Curing treatment is applied to the transparent resin 29. That is to say, the transparent resin 29 is irradiated with ultraviolet rays. A gap formed between the insertion hole H20 and the optical fiber 30 is extremely small. Therefore, it is not easy to irradiate the transparent resin 29 in the gap with ultraviolet rays.

However, the ferrule 20 has the groove T20 communicating with the insertion hole H20. Therefore, it is possible to efficiently irradiate the transparent resin 29 in the insertion hole H20 with ultraviolet rays from at least either one of the opening of the groove T20 on the first principal surface 20SA or the opening of the groove T20 on the side surface 20SS.

That is to say, the groove T20 is effective in not only disposing the transparent resin 29 in the insertion hole H20, but also irradiating the transparent resin 29 in the insertion hole H20 with ultraviolet rays.

In a case where the transparent resin 29 is a UV-and-thermosetting resin, heating treatment is applied to the transparent resin 29 at 100° C. for one hour, for example, after the transparent resin 29 is irradiated with ultraviolet rays.

A step of fixing the optical fiber 30 inserted into the insertion hole H20 with the transparent resin 29 can be surely performed without breaking the glass plate 22 and hence, the optical module 1 can be easily manufactured, and has high reliability.

The step S50 (resin injection step) may be performed after the step S60 (optical fiber insertion step).

Modification of First Embodiment

An optical module 1A of a modification of the first embodiment is similar to the optical module 1 and has substantially the same advantageous effects as the optical module 1. Constitutional elements having the same function as the constitutional elements of the optical module 1 are given the same reference symbols, and the repeated description will be omitted.

Figure 10:
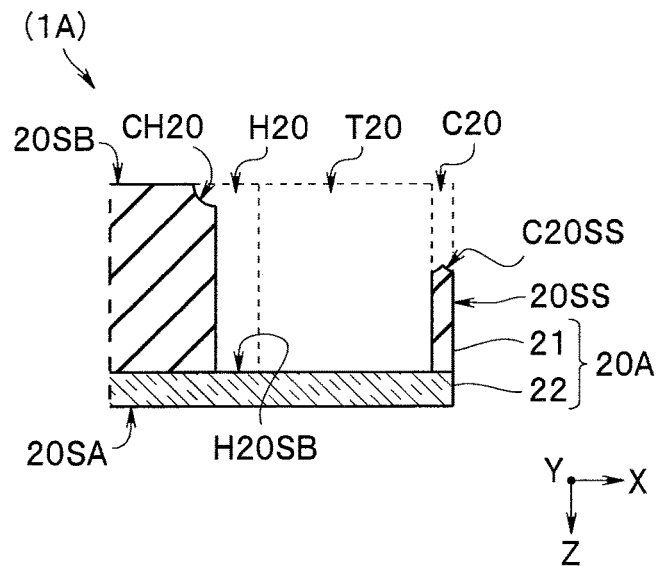
FIG. 10 is a cross-sectional view of an optical module of a modification of the first embodiment.

As shown in FIG. 10, in a ferrule 20A of the optical module 1A, an opening of the groove T20 on the side surface 20SS has an inclined surface (tapered surface) C20SS expanding toward the side surface 20SS.

An opening of the insertion hole H20 on the second principal surface 20SB also has an inclined surface CH20. That is to say, the opening of the insertion hole H20 on the second principal surface 20SB is larger than a bottom surface H20SB of the insertion hole. For example, an inner diameter of the opening of the insertion hole is 120 μm. In contrast, an inner diameter of the bottom surface H20SB of the insertion hole is 85 μn. The opening of the groove T20 on the second principal surface 20SB also has an inclined surface. A width of a principal surface opening is 90 μm. In contrast, a width of a bottom surface of the groove is 50 μm.

The inclined surface C20SS is formed in such a manner that a surface parallel to the second principal surface 20SB is formed by a step dicing method and, thereafter, isotropic etching is performed using sulfur hexafluoride (SF6), for example.

When the opening of the groove T20 on the side surface 20SS has the inclined surface C20SS, the transparent resin 29 can be easily injected from the side surface 20SS. Further, when the insertion hole H20 has the inclined surface CH20, the optical fiber 30 can be easily inserted.

Second Embodiment

An optical module 1B of a second embodiment is similar to the optical module 1, and has substantially the same advantageous effects as the optical module 1. Constitutional elements having the same function as the constitutional elements of the optical module 1 are given the same reference symbols, and the repeated description will be omitted.

Figure 11A:
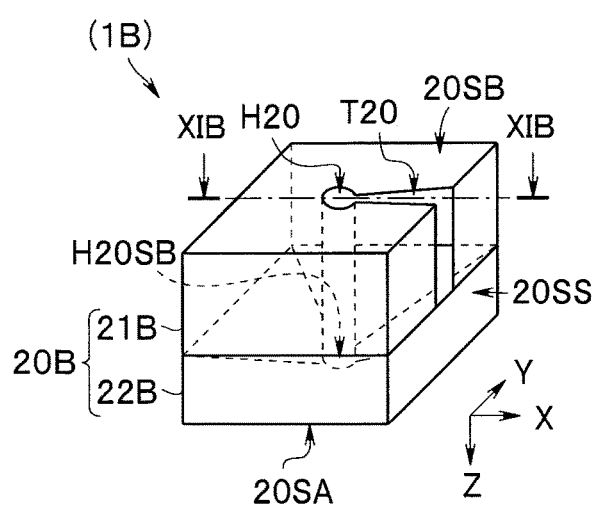
FIG. 11A is a perspective view of a ferrule of an optical module of a second embodiment.
Figure 11B:
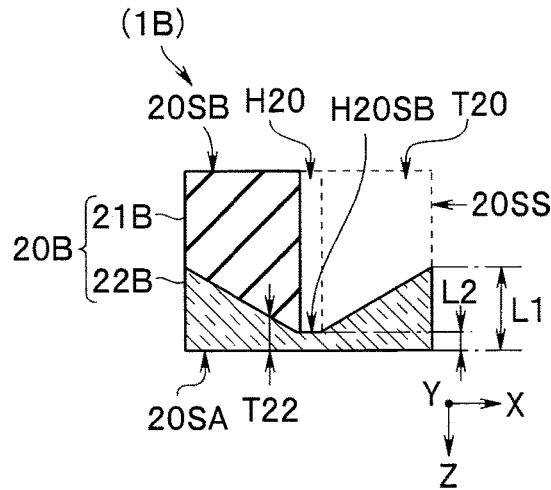
FIG. 11B is a cross-sectional view taken along line XIB-XIB in FIG. 11A.

In a ferrule 20B of the optical module 1B shown in FIG. 11A and FIG. 11B, not only the bottom surface H20SB of the insertion hole H20, but also whole of a bottom surface of the groove T20 is formed by glass 22B, being a transparent member.

As shown in FIG. 11B, a thickness T22 of the glass 22B linearly decreases from the side surface 20SS toward the bottom surface H20SB of the insertion hole H20. In the ferrule 20B, a first distance L1 between the opening of the groove T20 on the side surface 20SS and the first principal surface 20SA is greater than a second distance L2 between the bottom surface H20SB of the insertion hole H20 and the first principal surface 20SA.

Figure 12A:
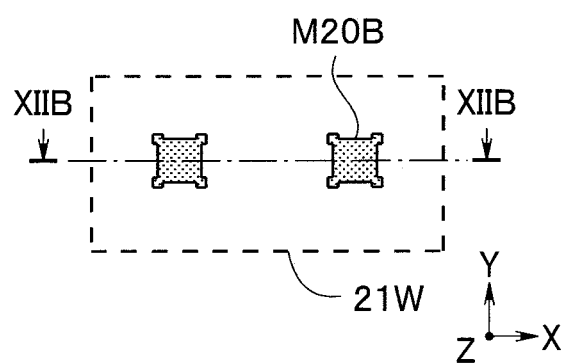
FIG. 12A is a top view for describing a method for manufacturing the ferrule of the optical module of the second embodiment.
Figure 12B:
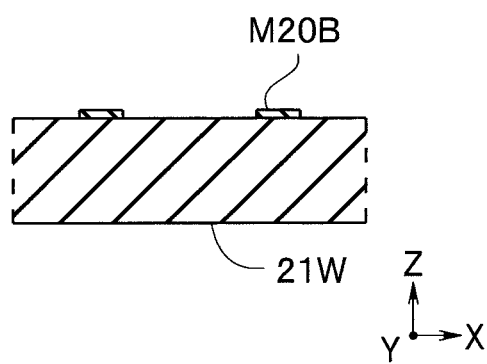
FIG. 12B is a cross-sectional view taken along line XIIB-XIIB in FIG. 12A.

In a method for manufacturing the ferrule 20B, as shown in FIG. 12A and FIG. 12B, etching masks M20B are disposed on a (100) surface of the silicon wafer 21W. Anisotropic wet etching is performed from the (100) surface using alkaline aqueous solution, such as KOH solution or TMAH (tetramethylammonium hydroxide) solution. In the anisotropic wet etching, an etching rate for the (100) surface is higher than an etching rate for a (111) surface.

Figure 13A:
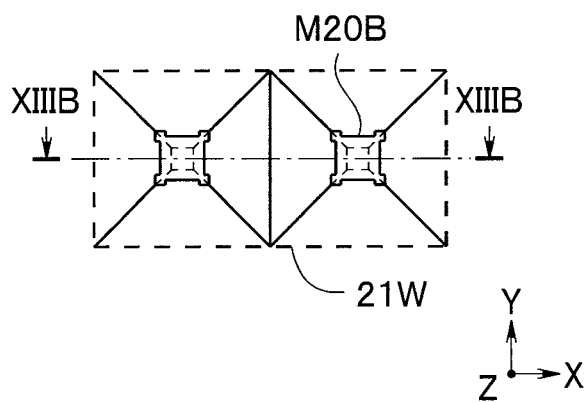
FIG. 13A is a top view for describing the method for manufacturing the ferrule of the optical module of the second embodiment.
Figure 13B:
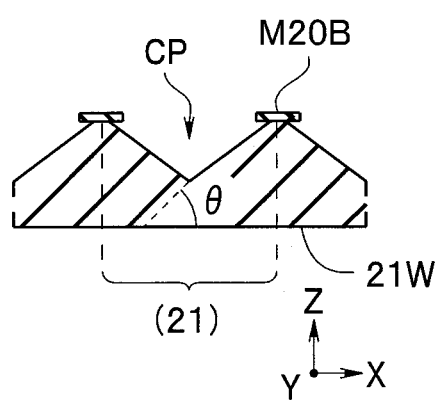
FIG. 13B is a cross-sectional view taken along line XIIIB-XIIIB in FIG. 13A.

Therefore, as shown in FIG. 13A and FIG. 13B, a recessed portion CP having a V shape in cross section is formed. An angle θ of a wall surface of the recessed portion CP is 54.7 degrees. That is to say, the recessed portion CP having four tapered surfaces is formed on the silicon wafer 21W by anisotropic wet etching.

Although the following steps are not shown in the drawing, after a transparent material, for example, molten glass, is caused to flow into the recessed portion CP of the silicon wafer 21W, the silicon wafer 21W is polished. With such operations, a bottom portion of the recessed portion CP is processed into the bottom surface H20SB of the insertion hole. The transparent material may also be a transparent resin.

The insertion hole H20 and the groove T20 are formed on a silicon surface of a wafer by reactive ion etching (RIE), the wafer being an integral body of glass and silicon, and the wafer is then cut into an individual ferrule 20B.

In the same manner as the optical module 1, in the optical module 1B, the transparent resin 29 can be easily injected from the opening on the side surface 20SS and can be easily cured by ultraviolet rays and hence, the optical module 1B has high reliability. Further, there is no possibility of the resin 50 flowing into the groove T20 and hence, there is no possibility of a reduction in transmission efficiency.

Third Embodiment

An optical module 1C of a third embodiment is similar to and has substantially the same advantageous effects as the optical modules 1, 1B and hence, constitutional elements having the same function as the constitutional elements of the optical modules 1, 1B are given the same reference symbols, and the repeated description will be omitted.

Figure 14:
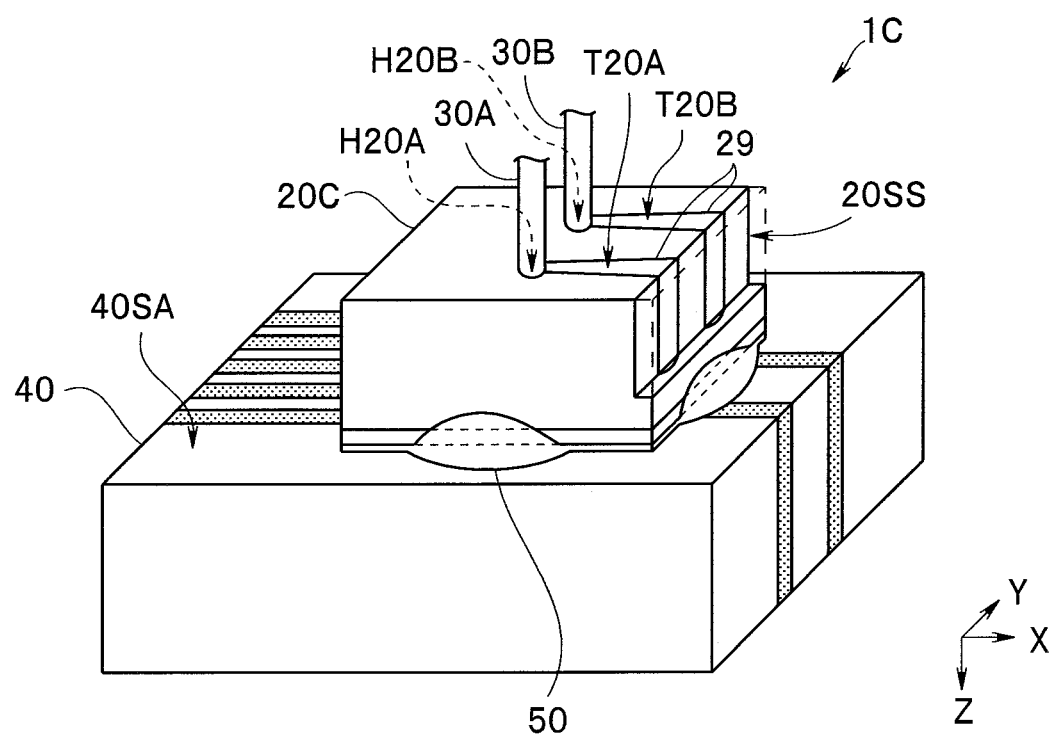
FIG. 14 is a perspective view of an optical module of a third embodiment.

The optical module 1C shown in FIG. 14 includes two light emitting elements (not shown in the drawing), two optical fibers 30A, 30B, and a ferrule 20C. The ferrule 20C has two insertion holes H20A, H20B and two grooves T20A, T20B. Each of the two grooves T20A, T20B extends to the side surface 20SS.

A first optical signal outputted from one light emitting element is transmitted through the optical fiber 30A. A second optical signal outputted from the other light emitting element is transmitted through the optical fiber 30B.

The optical module 1C has the advantageous effects of the optical module 1 and the like. The optical module 1C can transmit a greater amount of signal than the optical module 1 or the like. The optical module of the present invention may include three or more light emitting elements and three or more optical fibers.

As shown in FIG. 14, the resin 50 overflows onto the side surface 20SS only from a portion of a gap formed between the ferrule 20C and the wiring board 40. The resin 50 that locally spreads out onto the side surface 20SS particularly easily intrudes into the groove. However, in the optical module of the embodiment, there is no possibility of the resin 50 intruding into the groove.

The optical module of the present invention may have the configurations of the plurality of embodiments described above. For example, an opening on the side surface 20SS of the optical module 1C may have an inclined surface that expands toward the side surface 20SS as in the case of the optical module 1A.

Needless to say, endoscopes 5A to 5C including the optical modules 1A to 1C have the advantageous effects of the endoscope 5 and the advantageous effects of the optical modules 1A to 1C.

The present invention is not limited to the above-mentioned respective embodiments, and various changes, combinations, and applications are conceivable without departing from the gist of the invention.

What is claimed is:

1. An optical module for endoscope, the optical module comprising:
    a light emitting element including a light emitting circuit and an external electrode, the light emitting circuit being configured to convert an image pickup electric signal to an optical signal;
    a light guide member configured to transmit the optical signal;
    a holder including a first principal surface, a second principal surface, and a side surface, the first principal surface being made of a transparent material, the second principal surface being disposed on a side opposite to the first principal surface, the holder including a first bonded electrode and a second bonded electrode on the first principal surface, the second bonded electrode being connected to the first bonded electrode, the external electrode of the light emitting element being bonded to the first bonded electrode, the holder including an insertion hole into which the light guide member is inserted, the second principal surface including an opening of the insertion hole, a bottom surface of the insertion hole being made of the transparent material, the holder including a groove communicating with the insertion hole, the second principal surface including an opening of the groove, the side surface including an opening of the groove;
    a wiring board including a third principal surface, the wiring board including a third bonded electrode on the third principal surface, the third bonded electrode being bonded to the second bonded electrode of the holder; and
    a resin disposed between the first principal surface of the holder and the third principal surface of the wiring board, wherein
    in the holder, a first distance between the opening of the groove on the side surface and the first principal surface is greater than a second distance between the bottom surface of the insertion hole and the first principal surface.

2. The optical module for endoscope according to claim 1, wherein
    the resin covers a portion of the side surface, and does not intrude into the groove.

3. The optical module for endoscope according to claim 2, wherein
    a transparent resin is disposed between the light guide member and the insertion hole and in the groove.

4. The optical module for endoscope according to claim 1, wherein
    the wiring board is a three-dimensional wiring board including a recessed portion in which the light emitting element is accommodated.

5. The optical module for endoscope according to claim 1, wherein
    the resin is a thermosetting resin.

6. The optical module for endoscope according to claim 1, wherein
    the first distance is greater than the second distance by more than 100 μm.

7. The optical module for endoscope according to claim 1, wherein
    the resin is a thermosetting epoxy resin, and the first distance is greater than the second distance by more than 100 μm.

8. The optical module for endoscope according to claim 1, wherein
    the transparent material is glass.

9. The optical module for endoscope according to claim 1, wherein
    the holder includes the opening of the groove within a cutout on the side surface.

10. The optical module for endoscope according to claim 1, wherein
    the opening of the groove on the side surface includes an inclined surface expanding toward the side surface.

11. The optical module for endoscope according to claim 1, wherein
    whole of a bottom surface of the groove is made of the transparent material.

12. The optical module for endoscope according to claim 1, wherein
    a thickness of the transparent material decreases from the side surface toward the bottom surface of the insertion hole.

13. An endoscope that includes an optical module for endoscope, the optical module for endoscope comprising:
    a light emitting element including a light emitting circuit and an external electrode, the light emitting circuit being configured to convert an image pickup electric signal to an optical signal;

a light guide member configured to transmit the optical signal;

a holder including a first principal surface, a second principal surface, and a side surface, the first principal surface being made of a transparent material, the second principal surface being disposed on a side opposite to the first principal surface, the holder including a first bonded electrode and a second bonded electrode on the first principal surface, the second bonded electrode being connected to the first bonded electrode, the external electrode of the light emitting element being bonded to the first bonded electrode, the holder including an insertion hole into which the light guide member is inserted, the second principal surface including an opening of the insertion hole, a bottom surface of the insertion hole being made of the transparent material, the holder including a groove communicating with the insertion hole, the second principal surface including an opening of the groove, the side surface including an opening of the groove;

a wiring board including a third principal surface, the wiring board including a third bonded electrode on the third principal surface, the third bonded electrode being bonded to the second bonded electrode of the holder; and a resin disposed between the first principal surface of the holder and the third principal surface of the wiring board, wherein in the holder, a first distance between the opening of the groove on the side surface and the first principal surface is greater than a second distance between the bottom surface of the insertion hole and the first principal surface.

\* \* \* \* \*